United States Patent [19]

McFadden et al.

[11] 4,107,322

[45] Aug. 15, 1978

[54] BENZYL AND RELATED ESTERS OF 6,11-DIHYDRODIBENZ[B,E]OXEPIN-ACETIC ACIDS

[75] Inventors: Arthur R. McFadden, East Brunswick; Grover C. Helsley, Pottersville, both of N.J.

[73] Assignee: American Hoechst Corporation, Bridgewater, N.J.

[21] Appl. No.: 692,361

[22] Filed: Jun. 3, 1976

[51] Int. Cl.$^2$ ............................................ C07D 313/12
[52] U.S. Cl. ...................................... 424/278; 260/333
[58] Field of Search ......................... 260/333; 424/278

[56] References Cited

U.S. PATENT DOCUMENTS

| | | | |
|---|---|---|---|
| 3,678,077 | 7/1972 | Nakanishi et al. | 260/335 |
| 3,897,453 | 7/1975 | Gante et al. | 260/329.3 |
| 3,979,430 | 9/1976 | Nelson et al. | 260/338 |

FOREIGN PATENT DOCUMENTS 48,389  12/1972  Japan ....................................... 260/335

OTHER PUBLICATIONS

Chemical Abstracts, vol. 82 (1975) 170735d.
Chemical Abstracts, vol. 82 (1975) 170741c.
Chemical Abstracts, vol. 83 (1975) 97063x.
W. J. Hickinbottom, Reactions of Organic Compounds (1948), 2nd ed. pp. 98–100.

*Primary Examiner*—Norma S. Milestone
*Attorney, Agent, or Firm*—Curtis, Morris & Safford

[57] ABSTRACT

Benzyl and related esters of 6,11-dihydrodibenz[-b,e]oxepin-acetic and method for preparing same are described. These compounds are valuable as systemic and topical anti-inflammatory agents.

11 Claims, No Drawings

BENZYL AND RELATED ESTERS OF 6,11-DIHYDRODIBENZ[B,E]OXEPIN-ACETIC ACIDS

This invention relates to benzyl and related esters of 6,11-dihydrodibenz[b,e]oxepin-acetic acids which are useful as systemic and topical antiinflammatory agents.

To the best of our knowledge, the compounds of this invention have not heretofore been described. Precursors have been described by Helsley et al. in United States Patent Application Serial No. 459,774, filed Apr. 10, 1974 which is a continuation-in-part of Application Serial No. 394,801, filed Sept. 6, 1973, now abandoned, Ueno et al. in Belgian Patent No. 818,055 published Nov. 18, 1974 and Herbst et al. in United States Patent Application Serial No. 639,448, filed Dec. 10, 1975 which is a continuation-in-part of Application Serial No. 540,963, filed Jan. 14, 1975. While McFadden et al. in United States Patent Application Serial No. 600,210, filed July 30, 1975 describe 6,11-dihydrodibenz[b,e]oxepin-alkanoic acids and esters thereof, the valuable benzyl and related esters of the present invention are neither described nor suggested.

The compounds of the invention conform to the formula

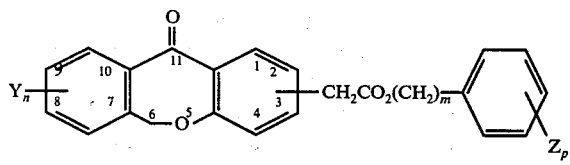

wherein Y and Z are hydrogen, alkyl of from 1 to 4 carbon atoms, alkoxy of from 1 to 4 carbon atoms, halogen or trifluoromethyl and $m$, $n$ and $p$ are each an integer from 1 to 3. Preferred compounds are those wherein the ester group is on the 2 or 3 position of the ring system, particularly those in which $m$ is 1 and Z is hydrogen.

The compounds of the present invention are prepared by esterifying a 6,11-dihydrodibenz[b,e]oxepin-acetic acid or an acid halide thereof with an alcohol of the formula

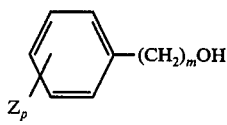

wherein Z, $p$ and $m$ are as defined earlier. Better yields are obtained by esterifying an acid halide. A preferred acid halide is the chloride prepared by reacting the corresponding acid disclosed in application Ser. No. 459,774 with phosphorus pentachloride or thionyl chloride in a benzene solvent and with a dimethylformamide catalyst. Esterification is preferably carried out in the presence of a chloroform solvent and an acid scavenger such as triethylamine.

The compounds of the present invention are useful as systemic antiinflammatory agents due to their ability to suppress systemic inflammation in mammals. This ability of the compounds is demonstrated in the carrageenin induced rat paw edema antiinflammatory assay [Proc. Soc. Exptl. Biol. Med., III, 544 (1962); J. Pharmacol. Exp. Ther., 141, 369 (1963)]. For example, an oral dose of 25 mg/kg of body weight of benzyl 6,11-dihydro-11-oxodibenz[b,e,]oxepin-2-acetate exhibits a 39% inhibition of edema. This datum illustrates that compounds of the invention are useful as antiinflammatory agents at a dose of from 0.1 to 100 mg/kg of body weight.

Compounds of the invention are also useful as topical antiinflammatory agents due to their ability to suppress dermal inflammation in mammals. This ability is demonstrated in the croton oil induced edema assay in mice [Endocrinology, 77, 625 (1965), Clin., Pharmacol., and Therap., 16 900 (1974)]. According to this assay a 42% decrease of this edema was caused by 2.0 mg of benzyl 6,11-dihydro-11-oxodibenz[b,e]-oxepin-2-acetate applied to the ear of a mouse in which said edema was induced. Similarly a 2.5 mg/ear dose of the same compound demonstrated an 87% decrease in edema. This data illustrates that compounds are useful as topical antiinflammatory agents at concentrations of from 0.1 to 20%.

Examples of compounds of the invention include:
benzyl 6,11-dihydro-9-methoxy-11-oxodibenz[b,e]-oxepin-3-acetate;
phenethyl 6,11-dihydro-10-methyl-11-oxodibenz[b,e]-oxepin-3-acetate;
4-fluorobenzyl 6,11-dihydro-10-fluoro-11-oxodibenz[b,e]oxepin-2-acetate;
3-(3-trifluoromethylphenyl)propyl-6,11-dihydro-8-trifluoromethyl-11-oxodibenz[b,e]oxepin-2-acetate;
4-chlorobenzyl 6,11-dihydro-11-oxodibenz[b,e]oxepin-3-acetate;
4-methoxyphenethyl 6,11-dihydro-8-methoxy-11-oxodibenz-[b,e]oxepin-2-acetate; and
4-ethylphenethyl 6,11-dihydro-11-oxodibenz[b,e]-oxepin-2-acetate.

The compounds of the present invention may be administered by any convenient route such as topically, orally, intramuscularly, subcutaneously or intraperitoneally. The preferred route of administration is topical.

For the purpose of topical administration, the active compounds of the invention may be incorporated into a solution, suspension, ointment, cream or salve. The preparations should contain at least 0.01% of active compound but may be varied to be between 0.05 and about 20% of the weight thereof. The amount of active compound in such compositions is such that an effective dosage will be obtained. Preferably, topically administerable preparations should contain between 0.1 and 10% by weight of active compound.

The topical compositions may also include water, fixed oils, polyethylene glycols, glycerol, petroleum, stearic acid, beeswax, other synthetic solvents or mixtures thereof; antibacterial agents such as benzyl alcohol or methyl paraben; antioxidants such as α-tocopherol acetate; chelating agents such as ethylenediaminetetraacetic acid; buffers such as acetates, citrates or phosphates; emulsifying agents such as polyoxethylene monooleate; and coloring materials and adjuvants such as ferric oxide or talc. The topical preparations can be enclosed in tubes, bottles, or jars made of metal, glass or plastic.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% by weight of active compound, but this may be varied depending upon the particular form and may conveniently be between 4% to about 70% of the weight of a dosage unit. The amount of active compound in such compositions is such that an effective dosage will be obtained. Preferred compositions and preparations according to the present invention are prepared so that an oral dosage unit form contains between about 1 and 500 milligrams of active compound.

Tablets, pills, capsules, troches, and the like may also contain a binder such as microcrystalline cellulose, gum tragacanth or gelatin; an excipient such as starch or lactose; a disintegrating agent such as alginic acid, Primogel, corn starch and the like; a lubricant such as magnesium stearate or Sterotex; a glidant such as colloidal silicon dioxide; and a sweetening agent such as sucrose or saccharin; or a flavoring agent such as peppermint, methyl salicylate, or orange flavoring. When the dosage unit form is in the form of a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings, and flavors. Materials used in preparing these various compositions should be pharmaceutically pure and non-toxic in the amounts used.

For the purpose of parenteral therapeutic administration, the active compounds of the invention may be incorporated in a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

Solutions or suspensions of the active compound may also include a sterile diluent such as water for injection, a saline solution, fixed oil, polyethylene glycol, glycerine, propylene glycol or other synthetic solvent; an antibacterial agent such as benzyl alcohol or methyl paraben; an antioxidant such as ascorbic acid or sodium bisulfite; a chelating agent such as ethylenediaminetetraacetic acid; a buffer such as an acetate, citrate or phosphate and an agent for the adjustment of tonicity such as sodium chloride or dextrose. The parenteral preparation can be enclosed in ampules, disposable syringes or multiple dose vials made of glass or plastic.

The invention is further illustrated by the following examples:

Experimental 4.00 g of phosphorus pentachloride are added with cooling to a solution of 6.0 g of 6,11-dihydro-11-oxodibenz[b,e]-oxepin-2-acetic acid in 70 ml of benzene. Fifteen minutes later a clear yellow solution forms. This is stirred at ambient temperature for 4 hours, and then the solvent is removed, leaving an amber oil. The oil is dissolved in 30 ml of chloroform and this solution is added dropwise to 70 ml of an ice-bath cooled mixture of 2.2 g of benzyl alcohol and 2.0 g of triethylamine. After total addition, the reaction mixture is stirred for 16 hours and then refluxed for 1 hour. The mixture is permitted to cool, washed successively with water, 1N hydrochloric acid, water, a 5% sodium hydroxide solution and water, dried and filtered. The filtered solution is concentrated, leaving an oil which solidifies to a light orange solid on standing. The solid is recrystallized from methanol to provide colorless crystals, mp 82°–84° C., of benzyl 6,11-dihydro-11-oxodibenz[b,e]oxepin-2-acetate.

Analysis:

Calculated for $C_{23}H_{18}C_4$: 77.08%C; 5.06%H. Found: 77.17%C; 5.24%H.

In a similar fashion 6,11-dihydro-11-oxodibenz[b,e]-oxepin-3-acetic acid is treated to provide benzyl 6,11-dihydro-11-oxodibenz[b,e]oxepin-3-acetate.

Similar treatments of 6,11-dihydro-10-methyl-11-oxodibenz[b,e]oxepin-2-acetic acid, 6,11-dihydro-8-fluoro-11-oxodibenz[b,e]oxepin-2-acetic acid, 6,11-dihydro-8-methoxy-11-oxodibenz[b,e]oxepin-2-acetic acid and 6,11-dihydro-9-trifluoromethyl-11-oxodibenz[b,e]oxepin-2-acetic acid yield benzyl 6,11-dihydro-10-methyl-11-oxodibenz[b,e]oxepin-2-acetate, benzyl 6,11-dihydro-8-fluoro-11-oxodibenz[b,e]oxepin-2-acetate, benzyl 6,11-dihydro-8-methoxy-11-oxodibenz[b,e]oxepin-2-acetate and benzyl 6,11-dihydro-9-trifluoromethyl-11-oxodibenz[b,e]oxepin-2-acetate, respectively.

Additionally, similar treatments of 6,11-dihydro-11-oxodibenz[b,e]oxepin-2-acetic acid with phenethyl alcohol, 3-phenylpropanol, 4-fluorobenzyl alcohol and 3-methoxybenzyl alcohol yield phenethyl 6,11-dihydro-11-oxodibenz[b,e]oxepin-2-acetate, 3-phenylpropyl 6,11-dihydro-11-oxodibenz[b,e]oxepin-2-acetate, 4-fluorobenzyl 6,11-dihydro-11-oxodibenz[b,e]oxepin-2-acetate and 3-methoxybenzyl 6,11-dihydro-11-oxodibenz[b,e]oxepin-2-acetate, respectively.

We claim:

1. A compound of the formula

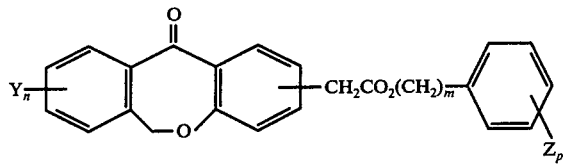

wherein Y and Z each represent hydrogen, alkyl of from 1 to 4 carbon atoms, alkoxy of from 1 to 4 carbon atoms, halogen or trifluoromethyl and m, n and p each is an integer from 1 to 3.

2. A compound of the formula

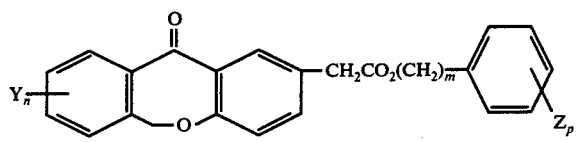

in which Y, Z, m, n and p are as defined in claim 1.

3. A compound of the formula

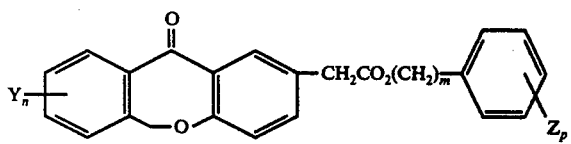

in which Y, Z, m, n and p are as defined in claim 1.

4. A compound as defined in claim 1 wherein n, m and p each is the integer 1.

5. A compound of the formula

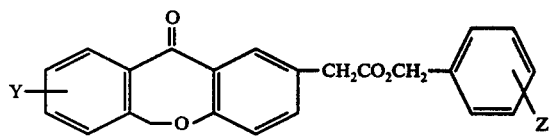

in which Y and Z are as defined in claim 1.

6. A compound of the formula

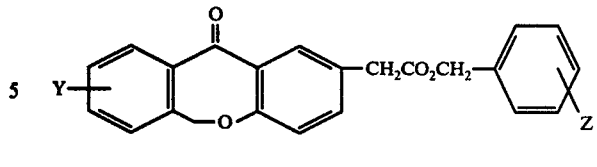

in which Y and Z are as defined in claim 1.

7. The compound defined in claim 1 which is benzyl 6,11-dihydro-11-oxodibenz[b,e]oxepin-2-acetate.

8. The compound defined in claim 1 which is benzyl 6,11-dihydro-11-oxodibenz[b,e]oxepin-3-acetate.

9. A method of treating, systemic inflammation which comprises orally or parenterally administering to a patient a pharmaceutically effective amount of a compound defined in claim 1.

10. A method of treating inflammation in the dermal layer of a patient which comprises topically administering to the inflamed area of the patient a pharmaceutically effective amount of a compound defined in claim 1.

11. A pharmaceutical composition suitable for treating inflammation which comprises between 7 and 70 percent by weight of a compound defined in claim 1 as an essential active ingredient, the balance being a pharmaceutically acceptable carrier therefor.

* * * * *

UNITED STATES PATENT AND TRADEMARK OFFICE
CERTIFICATE OF CORRECTION

PATENT NO. : 4,107,322
DATED : August 15, 1978
INVENTOR(S) : McFadden et al.

It is certified that error appears in the above-identified patent and that said Letters Patent are hereby corrected as shown below:

Abstract, lines 1 to 2, Column 2, lines 24 to 25 and line 33, and Column 4, lines 25 to 26, "...dibenz[-b,e]oxepin..." should be --...dibenz[b,e]oxepin...--;

Column 1, line 30, in the structural formula, the extreme left ring " 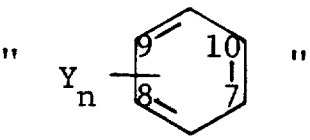 " should be -- 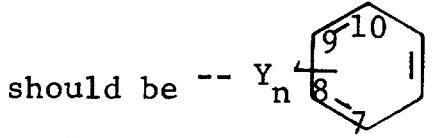 --;

line 55, "application" should be --Application--;

Column 2, line 13 and Column 3, line 63, "...dibenz[b,e]-oxepin-..." should be --...dibenz[b,e]oxepin-...--;

Claim 9, line 1, delete the comma (,) after "treating".

Signed and Sealed this

Seventeenth Day of July 1979

[SEAL]

Attest:

LUTRELLE F. PARKER
Attesting Officer    Acting Commissioner of Patents and Trademarks